May 26, 1942. W. E. LAMMERTS Plant Pat. 521
ROSE PLANT
Filed Oct. 14, 1941
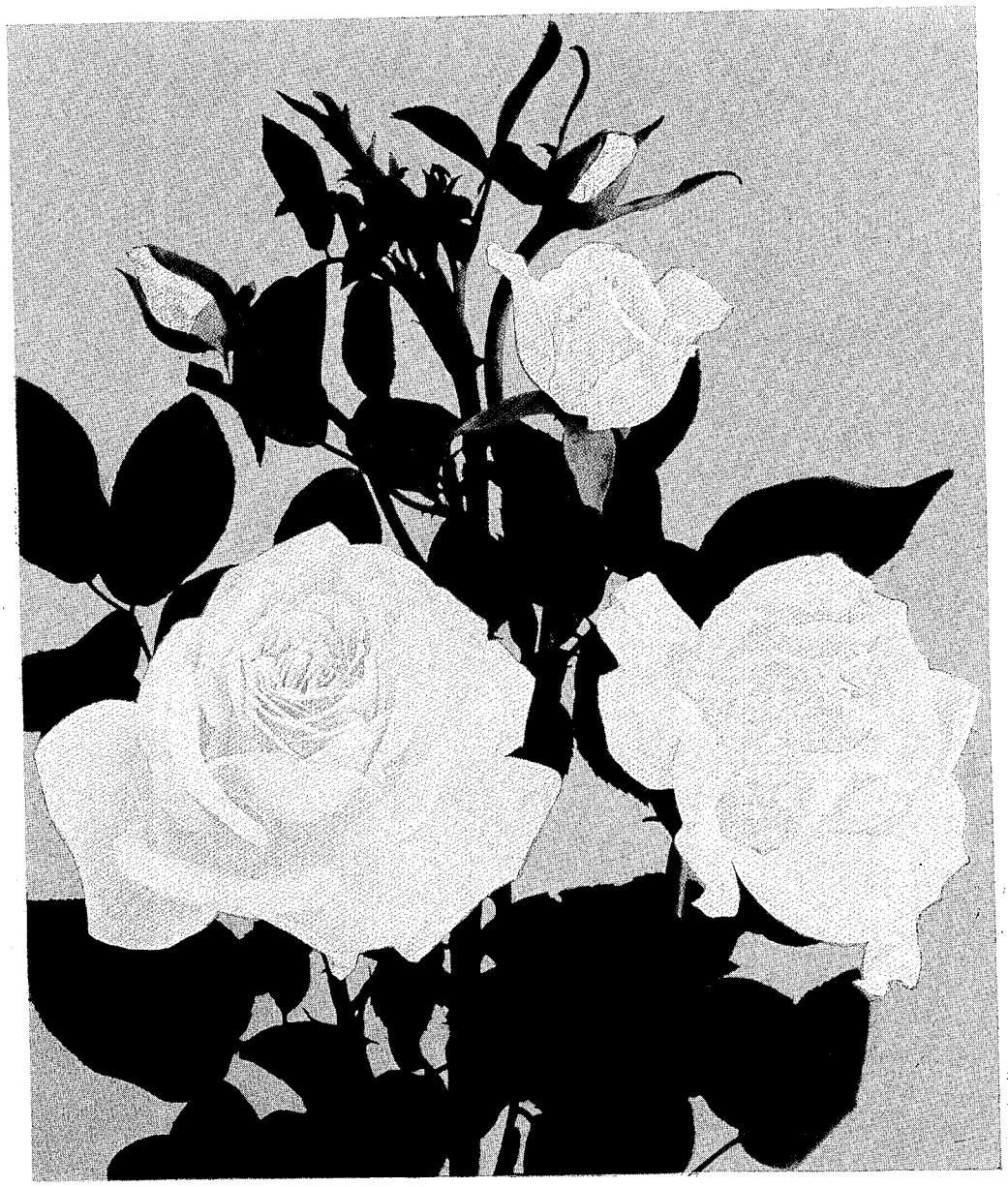
Inventor
Walter E. Lammerts
By Robert Robb
Attorneys Patented May 26, 1942

Plant Pat. 521

UNITED STATES PATENT OFFICE

521

ROSE PLANT

Walter E. Lammerts, Ontario, Calif., assignor to Armstrong Nurseries, Inc., Ontario, Calif., a corporation of California Application October 14, 1941, Serial No. 414,963

1 Claim. (Cl. 47—61)

The present invention relates to a new and distinct variety of rose plant originating as a seedling resulting from a cross of two well-known varieties, "Crimson Glory" (Plant Patent No. 105) and "Sister Therese."

As a result of crossing these varieties, one of the dark red range and the other of the yellow, a new variety, in the pink range, has been produced which, while distinct from either of its parents, possesses certain of the better qualities of each of them, the large size of the flower with ample petalage as well as its spreading manner of growth of "Crimson Glory," and the mildew resistance of its foliage and the style of its bud of "Sister Therese," respectively, being retained thereby.

Additionally, the vigor of growth of this new variety more nearly resembles that of "Sister Therese," although it is somewhat more vigorous even than the latter.

More specifically, the present rose is characterized as to novelty by the following distinguishing features:

(*a*) The unusual combination of color as shown in the accompanying color painting, which is described as giving the unusual bicolor effect of shrimp-pink and strawberry pink, which is extremely unusual in roses, if not unknown.

(*b*) The large size of the open flowers, usually in excess of three and one-half inches.

(*c*) The combination of tea and spicy fragrance which is quite strong.

(*d*) The very decided tendency to resistance to mildew.

(*e*) The unusual percentage of perfect flowers under average garden care.

(*f*) The quite spreading habit of growth and the thick heavy substance of the petals, which are extremely large on the outer portion of the flower.

The foregoing distinctions are more specifically referred to in the following detailed description, wherein all color terminology accords with Ridgway's Color Standard:

*Type*: Half hardy; dwarf; bush; outdoors; seedling; for cut flowers and garden decoration.

*Class*: Hybrid tea.

Seedling:

*Seed Parent.*—"Crimson Glory."

*Pollen Parent.*—"Sister Therese."

Propagation: Holds its distinguishing characteristics through succeeding propagations by budding.

*Flower*

Locality where grown: Ontario, California.

Flowers borne: Usually singly, sometimes several to stem in irregular cluster, on strong, medium to long stems.

Quantity of bloom: Moderate outdoors.

Continuity: Intermittent.

Fragrance: Fairly strong; combines tea and spicy.

Bud:

*Penduncle.*—Medium to long; medium to heavy; erect; stiff; near Cosse Green, Plate V; almost smooth; few gland-tipped cilia.

*Before calyx breaks.*—*Size*—Medium. *Form*—Ovoid with foliaceous appendages; some glandular bloom on the surface of the bud, with slender, much-cut foliaceous parts extending beyond the tip of the bud equal to three-fourths or more of its length.

*As calyx breaks.*—*Color*—from near Pomegranate Purple, Plate XII, to near Rocellin Purple, Plate XXXVIII. Inner surface with fine, woolly tomentum; both margins of two sepals lined with woolly tomentum; two with both margins lined with stipitate glands and one sepal with one margin lined with woolly tomentum and the other margin with stipitate glands.

*As first petal opens.*—*Size*—Medium. *Form*—ovoid. *Color*—outside—near Geranium Pink, Plate I, varying to near Rose Red, Plate XII, around outside margin changing to near Bittersweet Pink, Plate II, toward base to near Light Greenish Yellow, Plate V, around point of attachment. Inside—Grenadine Pink, Plate II, on top half changing to between Bittersweet Pink, Plate II, and Capucine Orange, Plate III, on lower half. Base around point of attachment near Lemon Yellow, Plate IV. *Opening*—opens up well.

Bloom:

*Size.*—When fully open, medium; 3½ inches to 4½ inches.

*Petalage.*—Double, from 30 to 35 petals arranged irregularly with few petaloids.

*Form.*—High center at first, becoming flat; petals remaining at first loosely rolled outward, becoming later, at maturity, tightly rolled outward.

Petals: Thick; leathery; with inside satiny; outside satiny but less than inside.

*Shape.*—Outside — very broadly obovate, scalloped with one, two, three or more notches. Intermediate — obovate. Inside—entirely obovate-cuneate; scalloped irregularly.

Color.—Colors may be modified by being blotched or tinted with other colors.

This description of a newly opened flower was made from a rose grown outdoors, during the month of July, 1941, at Ontario, California:

*Color.*—Outside petal:—outside surface—margin near Eosine Pink, Plate I, to near Bittersweet Pink, Plate II, in center to Light Greenish Yellow, Plate V, around point of attachment; inside surface—near Shell Pink, Plate XXVIII, around margin to near Capucine Buff, Plate III, in center to between Lemon Chrome, Plate IV, and Lemon Yellow, Plate IV, around point of attachment. Intermediate petal: outside surface—near Eosine Pink, Plate I, about margin to near Safrano Pink, Plate II, in middle to near Light Greenish Yellow, Plate V, around point of attachment; inside surface—near Shell Pink, Plate XXVIII, at tip to Near Flesh Color, Plate XIV, toward middle to between Lemon Chrome, Plate IV, and Lemon Yellow, Plate IV, around point of attachment. Inner petal: outside surface—near Eosine Pink, Plate I, around margin to between Safrano Pink, Plate II, and Grenadine Pink, Plate II, in middle to Light Greenish Yellow, Plate V, about point of attachment; inside surface—Flesh color, Plate XIV, except toward base around point of attachment where it is between Lemon Chrome, Plate IV, and Lemon Yellow, Plate IV.

This description was made from a rose that was open for three days outdoors in the month of July, 1941, at Ontario, California:

*Color.*—Outside petal: outside surface—near Cameo Pink, Plate XXVI, to Light Greenish Yellow, Plate V, around point of attachment; inside surface—between Pale Grayish Vinaceous, Plate XXXIX, and White, Plate LIII, to near Picric Yellow, Plate IV, around point of attachment. Inside petal: outside surface—between Rose Pink, Plate XII, and Deep Rose Pink, Plate XII, to near Pale Greenish Yellow, Plate V, around point of attachment; inside surface—near Cameo Pink, Plate XXVI, to near Martius Yellow, Plate IV, around point of attachment.

*General color effect.*—Newly opened flower—bicolor effect of Shrimp Pink, Plate I, and Strawberry Pink, Plate I. Three days open—near Shell Pink, Plate XXVIII, to near Pale Grayish Vinaceous, Plate XXXIX.

*Behavior.*—Drop off cleanly; fading; affected by hot, dry weather, i. e. becomes smaller in size and lighter in color than in cool weather.

*Flower longevity.*—On bush in garden—three days in July. Cut flowers grown outdoors and kept at living room temperatures four days in July.

*Reproductive organs*

Stamens: Many; arranged irregularly about pistils, mixed with petaloids.

Filaments: Medium to long; between Peach Red, Plate I, and Scarlet, Plate I, on inside filaments and from near Capucine Orange, Plate III, to near Buff Yellow, Plate IV, on outside filaments; few, without anthers.

Anthers: Large; near Buff Yellow, Plate IV, but edged with near Orange Chrome, Plate II, around suture lines; all open at once or nearly so.

Pollen: Moderate; near Baryta Yellow, Plate IV.

Pistils: Medium to many.

Styles: Very uneven; medium length; medium heavy; very bunched.

Stigma: Near Cinnamon, Plate XXIX.

Ovaries: Many protruding from calyx.

Sepals: Permanent; moderately long; recurved.

*Color.*—Inside—near Corydalis Green, Plate XLI. Outside—near Parrot Green, Plate VI.

Seeds: None observed.

*Plant*

Foliage:

*Leaves.*—Pinnate, compound of five sometimes seven leaflets; medium to large; leathery.

*Leaflets.*—Ovate lanceolate with apex acute; base round; margin simply serrate.

*Color.*—*Mature*—upper surface—Yew Green, Plate XXXI. Under surface—Asphodel Green, Plate XLI. *Young*—upper surface—margin near Anthracene Purple, Plate XLIV, blending gradually into Lincoln Green, Plate XLI, at mid-rib. Under surface—Neutral Red, Plate XXXVIII.

*Rachis.*—Medium heavy. Upper side—grooved; glandular. Under side—sparsely prickly.

*Stipules.*—Medium length; moderately narrow with medium long points, turning out at an angle of slightly more or less than 45°.

*Disease.*—Apparently resistant to mildew.

Growth:

*Habit.*—Bushy; spreading; much branched.

*Growth.*—Vigorous.

*Canes.*—Moderately heavy.

*Main stems.*—Near Rainette Green, Plate XXXI. *Large prickles*—many; medium length; straight with broad oval base; near Amber Brown, Plate III, tipped and marked at the base with Liver Brown, Plate XIV. *Small prickles*—few; near Amber Brown, Plate III, at the base blending gradually to near Sudan Brown, Plate III, at the tip. *Hairs*—none.

*Branches.*—Near Light Elm Green, Plate XVII. *Large prickles*—many; medium length; straight; vary at base from broad oval to narrow oval, the majority having a broad oval base; shades range from Russett, Plate XV, with blendings of Chestnut, Plate II, and Liver Brown, Plate XIV, at the base and tip to prickles of a light even shade of near Sudan Brown, Plate III. *Small prickles*—few; base near Amber Brown, Plate III, tipped Auburn, Plate II. *Hairs*—to the naked eye there are no hairs either setaceous or ciliate. Under a strong magnifying glass a fuzzy bloom may be seen.

*New shoots.*—Near Rainette Green, Plate XXXI, at the tip end of new shoots, on the sunny side, the color blends gradually into a Yellowish Oil Green, Plate V. The under side (side not exposed to so much sun) is fairly uniformly Rainette Green, Plate XXXI. *Large prickles*—many; medium length; straight; with narrow base; near Maroon, Plate I, in some cases blending gradually into near Citrine, Plate IV, at base and occasionally blending at the extreme tip into near Citrine. *Small prickles*—few; to the naked eye the small prickles are near Maroon, Plate I, but under the magnifying glass the near Maroon blends gradually into near Lime Green, Plate XXXI, at the base. *Hairs*—occasional gland-tipped cilia.

I claim:

A new and distinct rose plant of the hybrid tea class, characterized as to novelty by its vigorous, spreading habits of growth; the decided resistance to mildew of its foliage; the large size and perfection of its flowers under average garden care; the unusual combination of colors and thick, heavy substance of the petals of these flowers; and the strong combination of tea and spicy fragrance thereof, substantially as shown and described.

WALTER E. LAMMERTS.